(12) United States Patent
Italiaie et al.

(10) Patent No.: US 11,350,969 B1
(45) Date of Patent: Jun. 7, 2022

(54) ROTATABLE SPINAL IMPLANT, SYSTEM, AND METHOD

(71) Applicant: Warsaw Orthopedic, Inc., Warsaw, IN (US)

(72) Inventors: Christel Italiaie, Memphis, TN (US); Leigh A. Folger, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/165,441

(22) Filed: Feb. 2, 2021

(51) Int. Cl.
*A61B 17/70* (2006.01)
*A61B 17/86* (2006.01)

(52) U.S. Cl.
CPC ...... *A61B 17/7032* (2013.01); *A61B 17/7049* (2013.01); *A61B 17/8665* (2013.01)

(58) Field of Classification Search
CPC ............ A61B 17/7032; A61B 17/7049; A61B 17/8665
USPC ........ 606/264, 265, 267, 269, 270, 272, 278
See application file for complete search history.

(56) References Cited

U.S. PATENT DOCUMENTS

| | | | |
|---|---|---|---|
| 6,277,120 B1 | 8/2001 | Lawson | |
| 7,166,108 B2 | 1/2007 | Mazda et al. | |
| 7,481,828 B2 | 1/2009 | Mazda et al. | |
| 7,572,277 B2 | 8/2009 | Roussouly et al. | |
| 7,655,025 B2 | 2/2010 | Ritland | |
| 7,717,938 B2 | 5/2010 | Kim et al. | |
| 7,803,174 B2 | 9/2010 | Denis et al. | |
| 7,806,912 B2 | 10/2010 | Lawton et al. | |
| 7,867,255 B2 | 1/2011 | Miller et al. | |
| 7,942,901 B2 | 5/2011 | Rezach | |
| 7,959,654 B2 | 6/2011 | Mazda et al. | |
| 8,021,399 B2 | 9/2011 | Ritland | |
| 8,162,946 B2 | 4/2012 | Baccelli et al. | |
| 8,172,843 B2 | 5/2012 | Baccelli et al. | |
| 8,236,028 B2 | 8/2012 | Kalfas et al. | |
| 8,246,657 B1 | 8/2012 | Samuel | |
| 8,298,269 B2 | 10/2012 | Null et al. | |
| 8,323,319 B2 | 12/2012 | Mazda et al. | |
| 8,372,119 B2 | 2/2013 | Kim et al. | |
| 8,430,916 B1 | 4/2013 | Winslow et al. | |
| 8,430,918 B2 | 4/2013 | Baccelli et al. | |
| 8,715,323 B2 | 5/2014 | Ballard et al. | |
| 8,852,237 B2 | 10/2014 | Kalfas et al. | |
| 8,870,870 B2 | 10/2014 | Baccelli et al. | |

(Continued)

*Primary Examiner* — Eduardo C Robert
*Assistant Examiner* — David C Comstock
(74) *Attorney, Agent, or Firm* — Fox Rothschild LLP; P. Marshall Ticer

(57) ABSTRACT

A construct may include a connector having a first body portion and a second body portion rotatably coupled to another. A first implant cavity may be defined, at least partly, by at least two threaded arm portions defining a first axis between the at least two threaded arm portions. The first implant cavity may include a first receiving cavity configured to adjustably orient a first rod in a plane substantially perpendicular to the first axis, and the second implant cavity may include a second receiving cavity configured to orient a second rod. In some embodiments, the threaded arm portions are configured to receive a first set screw such that when the first set screw is fully tightened along the first axis the first rod is fixed relative to the first body portion in a direction extending substantially parallel with the plane.

17 Claims, 11 Drawing Sheets

(56) References Cited

U.S. PATENT DOCUMENTS

| | | |
|---|---|---|
| 8,926,668 B2 | 1/2015 | Douget |
| 8,936,625 B2 | 1/2015 | Larroque-Lahitette et al. |
| 8,940,020 B2 | 1/2015 | Rathbun |
| 8,961,572 B2 | 2/2015 | Kim et al. |
| 8,998,957 B2 | 4/2015 | Kalfas et al. |
| 8,998,961 B1 | 4/2015 | Ziemek et al. |
| 9,101,405 B2 * | 8/2015 | Dickinson .......... A61B 17/7055 |
| 9,492,205 B2 | 11/2016 | Alsup et al. |
| 9,918,748 B2 | 3/2018 | Kalfas et al. |
| 9,980,755 B2 | 5/2018 | Murray et al. |
| 10,238,432 B2 | 3/2019 | Carruth et al. |
| 10,251,678 B2 | 4/2019 | Alsup et al. |
| 10,383,663 B2 | 8/2019 | Murray et al. |
| 2005/0131404 A1 | 6/2005 | Mazda et al. |
| 2005/0171537 A1 | 8/2005 | Mazel et al. |
| 2006/0079892 A1 | 4/2006 | Roychowdhury et al. |
| 2007/0270817 A1 | 11/2007 | Rezach |
| 2008/0140124 A1 | 6/2008 | Jeon et al. |
| 2009/0228046 A1 | 9/2009 | Garamszegi |
| 2010/0049253 A1 * | 2/2010 | Miller ................ A61B 17/7038 606/264 |
| 2010/0249845 A1 | 9/2010 | Meunier et al. |
| 2010/0280552 A1 | 11/2010 | Lee |
| 2011/0172717 A1 * | 7/2011 | Miller .................. A61B 17/705 606/279 |
| 2011/0190828 A1 * | 8/2011 | Null .................... A61B 17/7041 606/279 |
| 2011/0301644 A1 | 12/2011 | Belliard |
| 2012/0029571 A1 | 2/2012 | Schwab et al. |
| 2012/0158064 A1 | 6/2012 | Kroll |
| 2012/0271354 A1 | 10/2012 | Baccelli et al. |
| 2012/0303121 A1 | 11/2012 | Douget et al. |
| 2013/0096617 A1 * | 4/2013 | Ballard .............. A61B 17/7049 606/278 |
| 2014/0094850 A1 | 4/2014 | Clement et al. |
| 2014/0336706 A1 | 11/2014 | Garamszegi |
| 2017/0281237 A1 | 10/2017 | Murray et al. |
| 2017/0281246 A1 | 10/2017 | Murray et al. |
| 2017/0281247 A1 * | 10/2017 | Murray ............. A61B 17/7004 |
| 2018/0098798 A1 | 4/2018 | Italiaie et al. |
| 2018/0125538 A1 | 5/2018 | Daniels et al. |
| 2018/0280062 A1 | 10/2018 | Lee et al. |
| 2018/0280063 A1 | 10/2018 | Lee et al. |
| 2019/0175226 A1 | 6/2019 | Carruth et al. |
| 2019/0321083 A1 | 10/2019 | Murray et al. |

* cited by examiner

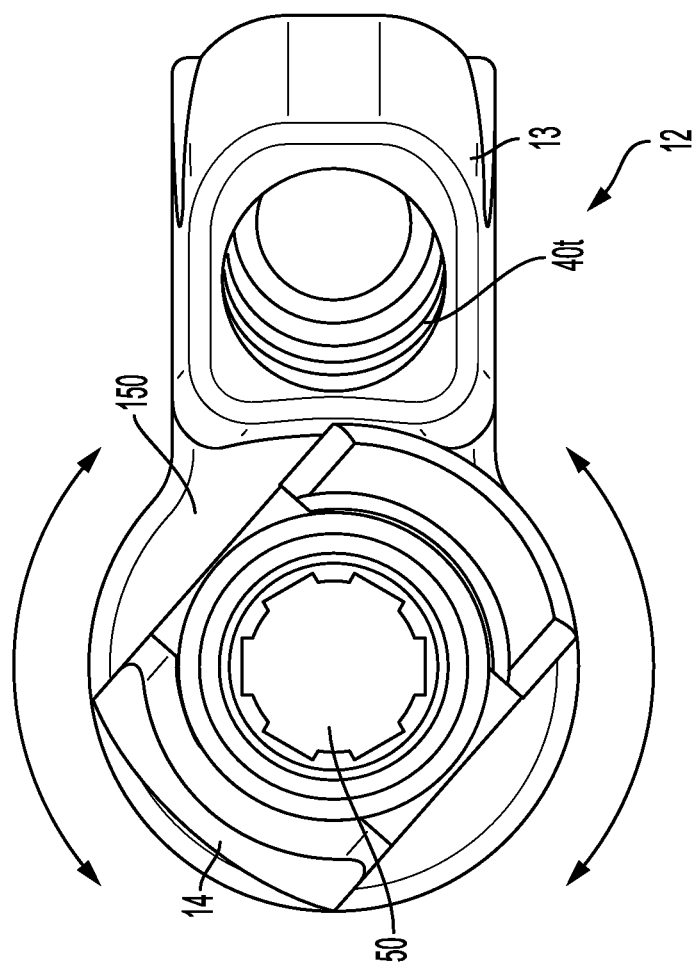
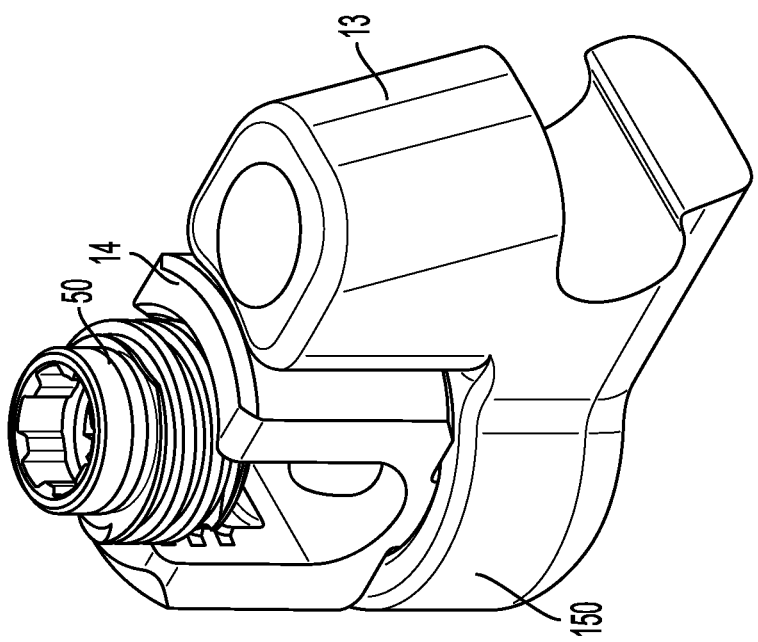
FIG. 8B
FIG. 8A

ROTATABLE SPINAL IMPLANT, SYSTEM, AND METHOD

CROSS-REFERENCE TO RELATED U.S. PATENT APPLICATION

This Application hereby incorporates the disclosure of U.S. patent application Ser. No. 16/395,498, titled SPINAL IMPLANT SYSTEM AND METHOD, filed Apr. 26, 2019, into this document by reference in its entirety.

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis, kyphosis, and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members.

Conventional surgery may often involve a plurality of connectors that are attached to corresponding pedicle screws in a series of vertebrae. Conventional connectors are only capable of fixing the rod in a single orientation and do not allow the rod to pivot. That is to say, the rod, connector, and pedicle screw fix the rod system in a single extension direction. In some initial surgeries, and in some revision surgeries, a fixed system is disadvantageous because a fixed system may not provide a surgeon and/or patient with sufficient range of motion to obtain a target alignment.

SUMMARY

In one aspect, a spinal construct including a connector comprising a first body portion and a second body portion is disclosed. The first body portion may be rotatably coupled to the second body portion, the first body portion may have a first implant cavity and the second body portion may have a second implant cavity. The first implant cavity may be defined, at least partly, by at least two threaded arm portions defining a first axis between the at least two threaded arm portions. The first implant cavity may include a first receiving cavity configured to adjustably orient a first rod in a plane substantially perpendicular to the first axis, and the second implant cavity may include a second receiving cavity configured to orient a second rod. In some embodiments, the threaded arm portions are configured to receive a first set screw such that when the first set screw is fully tightened along the first axis the first rod is fixed relative to the first body portion in a direction extending substantially parallel with the plane. In some embodiments, the second body portion may further include a threaded opening communicating with the second receiving cavity, the threaded opening may define a second axis and be configured to receive a second set screw such that when the second set screw is fully tightened the second rod is fixed relative to the second body portion.

In another aspect, the first axis and the second axis may extend in different directions, and the first rod and the second rod may be extendable in different directions.

In another aspect, the first axis and the second axis may be disposed in a non-perpendicular orientation relative to one another, and the first rod and the second rod may extend in a non-perpendicular orientation relative to one another.

In another aspect, the first body portion may further include an aperture disposed proximate a bottom surface of the first body portion, the second body portion may further include a channel and a column, and the column may be disposed proximate a central portion of the channel. The column may extend through the aperture and the bottom surface of the first body portion may be disposed within the channel.

In another aspect, a retaining clip may be further provided. In some embodiments, the first body portion further includes a first groove, and the first groove may be disposed proximate the bottom surface. The second body portion may further include a second groove, the second groove may be disposed on an interior sidewall of the second body portion and face the channel, for example. The retaining clip may be seated in the first groove and the second groove, and the retaining clip may rotatably couple the first body portion and the second body portion.

In another aspect, the first body portion may further include a first lateral sidewall and a second lateral sidewall opposite the first lateral sidewall, the first and second lateral sidewalls may be substantially planar and extend in a vertical direction, for example. The first body portion may further include a first curved sidewall and a second curved sidewall opposite the first curved sidewall, the first and second curved sidewalls may extend between the first lateral sidewall and the second lateral sidewall, for example. In some embodiments, the first receiving cavity may extend in a direction that is substantially perpendicular to the vertical direction.

In another aspect, the first body portion may further include an aperture extending through a bottom surface of the first body portion. The second body portion may further include a channel and a threaded column, the threaded column may be disposed proximate a central portion of the channel, and the threaded column may extend through the aperture and the bottom surface of the first body portion may be disposed within the channel.

In another aspect, a nut may be further provided. The nut may be engaged with the threaded column and configured to retain the first body portion relative to the second body portion in the vertical direction.

In another aspect, a spline may be further provided. When the nut is fully tightened the spline may fixedly engage the first body portion relative to the second body portion, for example.

In another aspect, a spinal construct is disclosed. The spinal construct may include a connector comprising a first body portion rotatably coupled to a second body portion. The first body portion may include a plurality of teeth disposed on a lip portion, the second body portion may include a plurality of grooves, and the grooves may correspond to the plurality of teeth. The first body portion may include a first implant cavity and the second body portion may include a second implant cavity. The first implant cavity may be defined, at least partly, by at least two threaded arm portions defining a first axis between the at least two threaded arm portions. The first implant cavity may include a first receiving cavity configured to adjustably orient a first rod in a plane substantially perpendicular to the first axis, and the second implant cavity may include a second receiving cavity configured to orient a second rod. In some embodiments, the threaded arm portions may be configured to receive a first set screw such that when the first set screw is fully tightened along the first axis the first rod is fixed relative to the first body portion in a direction extending substantially parallel with the plane. In some embodiments, the second body portion may further include a threaded opening communicating with the second receiving cavity, the threaded opening may define a second axis and be configured to receive a second set screw such that when the second set screw is fully tightened the second rod is fixed relative to the second body portion, for example.

In another aspect, the plurality of teeth may be arranged symmetrically with respect to one another on the lip portion, for example.

In another aspect, the plurality of grooves may be arranged as a segment of a circle and symmetrically disposed with respect to one another on the second body portion, for example.

In another aspect, the first axis and the second axis may extend in different directions, and the first rod and the second rod are extendable in different directions, for example.

In another aspect, the first axis and the second axis may be disposed in a non-perpendicular orientation relative to one another, and the first rod and the second rod may extend in a non-perpendicular orientation relative to one another, for example.

In another aspect, the first body portion may further include a first lateral sidewall and a second lateral sidewall opposite the first lateral sidewall, and the first and second lateral sidewalls may be substantially planar and extend in a vertical direction. The first body portion may also further include a first curved sidewall and a second curved sidewall opposite the first curved sidewall, and the first and second curved sidewalls may extend between the first lateral sidewall and the second lateral sidewall. In some embodiments, the first receiving cavity extends in a direction that is substantially perpendicular to the vertical direction.

In another aspect, the first body portion may further include an aperture extending through the bottom surface of the first body portion. Additionally, the second body portion may further include a channel and a threaded column, the threaded column may be disposed proximate a central portion of the channel, for example. Additionally, the threaded column may extend through the aperture, and the bottom surface of the first body portion may be disposed within the channel.

In another aspect, a nut may be further provided. The nut may be engaged with the threaded column and configured to retain the first body portion relative to the second body portion in the vertical direction, for example.

In another aspect, a spinal construct system is disclosed. The spinal construct system may include at least one anchoring member configured to couple to a corresponding pedicle screw and a plurality of connectors. Each connector may include a first body portion and a second body portion, and the first body portion may be rotatably coupled to the second body portion, for example. The first body portion may have a first implant cavity and the second body portion may have a second implant cavity. Each first implant cavity may be defined, at least partly, by at least two corresponding threaded arm portions defining a corresponding first axis between the at least two corresponding threaded arm portions, for example. Each first implant cavity may include a corresponding first receiving cavity configured to adjustably orient a first rod in a range of extension directions substantially perpendicular to the first axis, and each second implant cavity may include a corresponding second receiving cavity configured to orient a second rod, for example. In some embodiments, each of the corresponding threaded arm portions may be configured to receive a corresponding first set screw such that when the corresponding first set screw is fully tightened along the corresponding first axis the first rod is fixed relative to the corresponding first body in a direction comprising the range of extension directions. In some embodiments, each second body portion may further include a corresponding threaded opening communicating with the corresponding second receiving cavity, each threaded opening may define a corresponding second axis and be configured to receive a corresponding second set screw such that when the corresponding second set screw is fully tightened the second rod is fixed relative to the corresponding body.

In another aspect, the first body portion may further include an aperture disposed proximate a bottom surface of the first body portion, and the second body portion may further include a channel and a column, the column may be disposed proximate a central portion of the channel, for example. Additionally, the column may extend through the aperture, and the bottom surface of the first body portion may be disposed within the channel, for example.

In another aspect, a spline, a nut, and a threaded column, may be further provided. In some embodiments, when the nut is fully tightened the spline may fixedly engage the first body portion relative to the second body portion.

BRIEF DESCRIPTION OF THE DRAWINGS

The present disclosure will become more readily apparent from the specific description accompanied by the following drawings, in which:

FIG. 8A is a perspective view of an example spinal implant connector in accordance with the principles of the present disclosure;

FIG. 8B is a top down view of the example spinal implant connector of FIG. 8A in accordance with the principles of the present disclosure;

DETAILED DESCRIPTION

Figure 1:
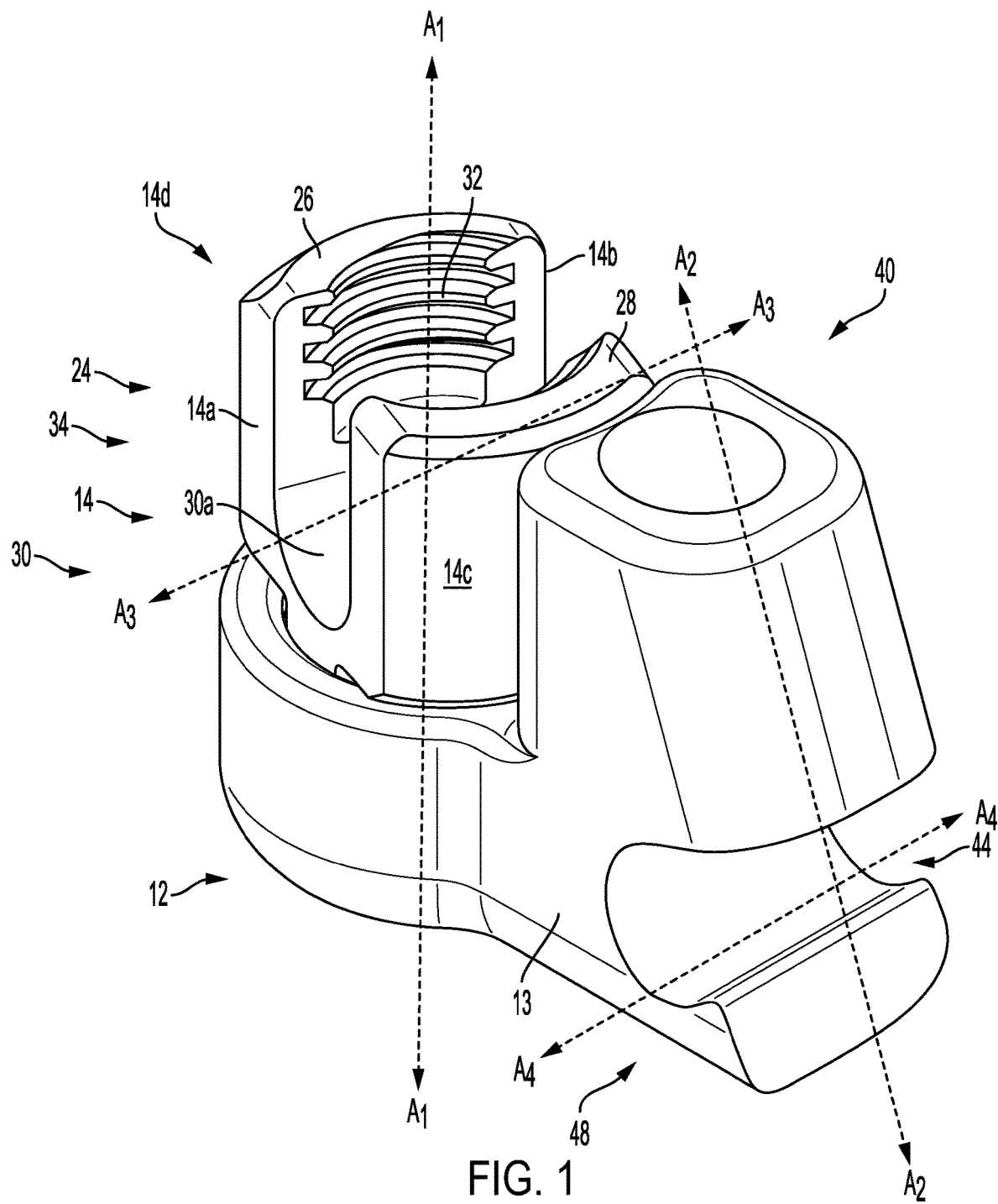
FIG. 1 is a perspective view of a spinal implant connector in accordance with the principles of the present disclosure.
Figure 2:
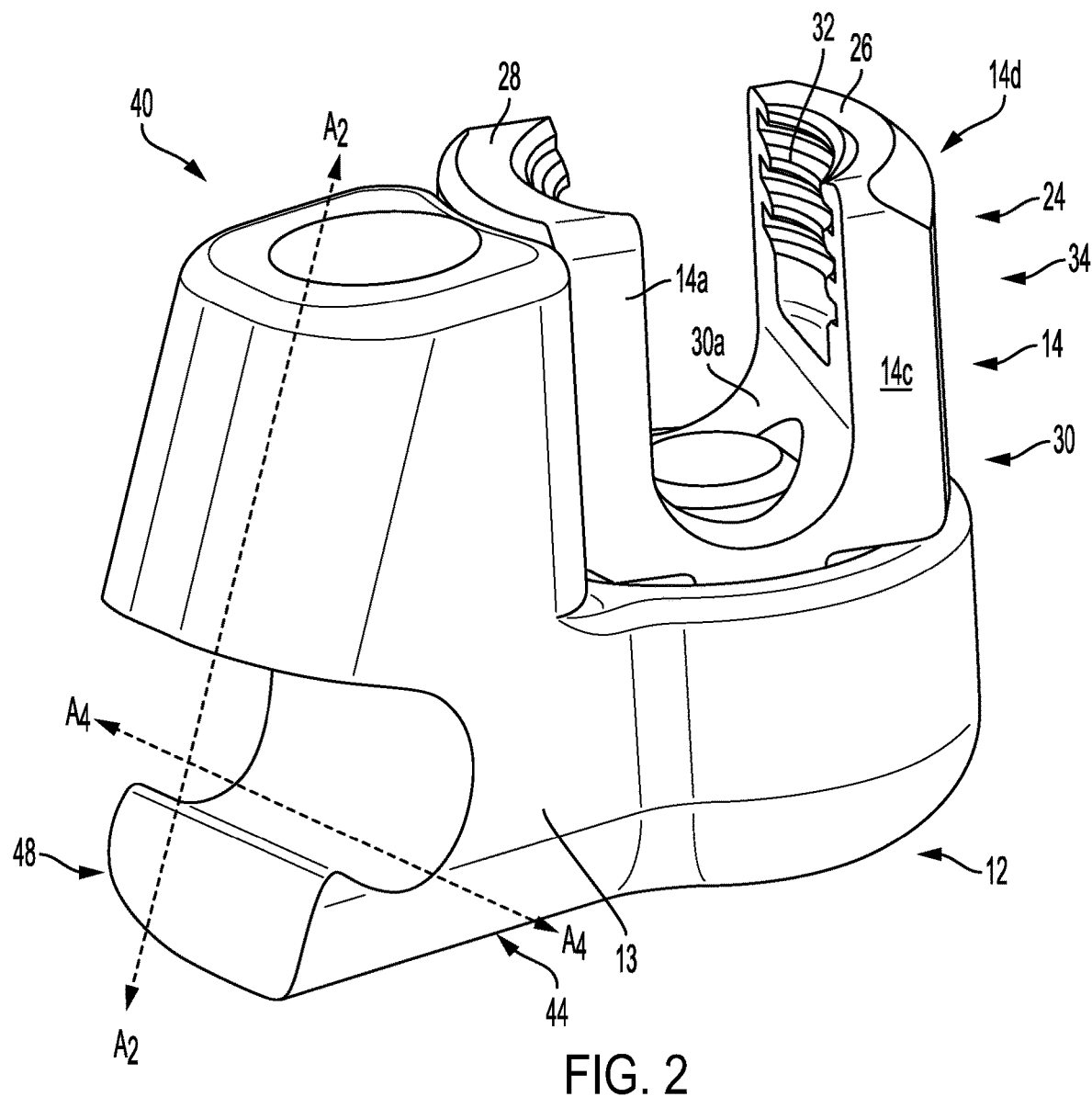
FIG. 2 is an alternate perspective view of a spinal implant connector in accordance with the principles of the present disclosure.
Figure 3:
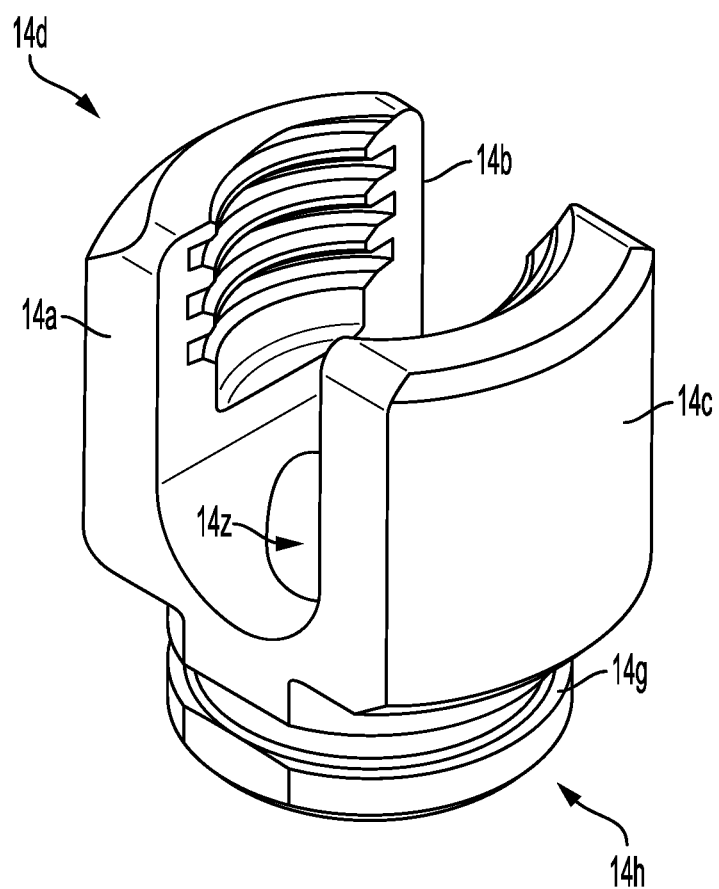
FIG. 3 is a perspective view of a first body portion of a spinal implant connector in accordance with the principles of the present disclosure.

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the systems and methods of the present disclosure are employed with a revision surgery to correct or otherwise assist with a previous surgery. At least one example previous surgery may include the installation of a plurality of pedicle screws in adjacent vertebrae of a patient's spine. Each of the plurality of pedicle screws may be coupled to a corresponding anchoring member configured to receive a longitudinal rod and orient the longitudinal rod in a direction corresponding to a target alignment of the patient's spine. Unfortunately, in some instances, the overall alignment of the longitudinal rod may have shifted away from the intended target alignment. Such shifting may occur to due to trauma to the patient's spine, aging of the patient, and/or mechanical failure of any of the previously installed parts. In these instances, the patient may undergo a revision procedure where a second set of pedicle screws may be installed in adjacent vertebrae of the patient's spine. For example, a second array of new pedicle screws may be installed in addition to the previously installed pedicle screws. The second set of pedicle screws may be coupled to a second set of anchoring members that are in turn coupled to a second longitudinal rod. In these revision surgeries, a connector may be used to connect the first longitudinal rod to the second longitudinal rod and thereby bring the alignment of the patient's spine back into the target alignment (or at least improve the patient's current spinal alignment). The present disclosure describes a spinal construct including a connector that enables the adjustment of the orientation of a longitudinal rod within a retaining portion of the connector.

For example, spinal constructs and connectors in accordance with the present disclosure provide a means to fixedly attach a first longitudinal rod to a first retaining portion of a connector and place the second longitudinal rod in a second retaining portion of the connector where at least one of the longitudinal rods may be positioned in a range of orientations with respect to the connector. For example, an orientation or extension direction of the first longitudinal rod may be adjustable within a corresponding retaining portion of the connector. In this way, the present disclosure describes a connector having at least one retaining portion for receiving a rod that may fix the rod in a range of orientations with respect to the connector.

In some embodiments, the present surgical system includes a spinal construct having a connector. In some embodiments, the connector may include a tulip hybrid crosslink connector. In some embodiments, the connector includes a top loading spinal rod passageway and a side loading spinal rod passageway. The connector may be configured to connect a spinal rod with a spinal construct including, such as, for example, bone screws and a spinal rod. In some embodiments, the connector includes a first implant cavity and a second implant cavity. In some embodiments, at least one of the implant cavities is configured for side loading a spinal rod. In some embodiments, the connector includes an opening communicating with the first implant cavity and an opening communicating with the second implant cavity. In some embodiments, the first implant cavity may be rotatable with respect to the connector.

In some embodiments, one or all of the components of the surgical system may be disposable, peel-pack, pre-packed sterile devices. One or all of the components of the system may be reusable. The system may be configured as a kit with multiple sized and configured components. For example, shims and inserts may also be provided for further facilitating the securement of the longitudinal rods. Similarly, various sized and types of set screws may be provided for various types and orientations of longitudinal rods.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures.

Referring generally to FIGS. 1-8B, there are illustrated components of a spinal implant connector 12. Referring generally to FIGS. 9A-10B, there are illustrated components of a similar spinal implant connector 12z. The connectors 12 and 12z may be used as part of a surgical system, such as, for example, a spinal implant system 10 illustrated in FIG. 11.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyethermide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 comprises a spinal construct including a spinal implant connector 12, 12a. In some embodiments, connector 12 is configured to connect a first longitudinal rod 150 with bone screws 160 and a second longitudinal rod 152, (see FIG. 11). In some embodiments, the orientation of first longitudinal rod 150 may be adjustable, at least partly, and with respect to connector 12.

Connector 12 may include a two part body comprising a first body portion 14 and a second body portion 13, e.g., a multicomponent body. In at least one embodiment, first and second body portions 13 and 14 are each formed of a single component material that is machined to include various contours, structural features, relationships, and/or functional geometry. In various embodiments, the first body portion 14 may be rotatably coupled to the second body portion 13, as will be explained in further detail below. First body portion 14 may include a first lateral surface 14a and a second lateral surface 14b opposite first lateral surface 14a. The first and second lateral surfaces 14a and 14b may be substantially planar surfaces extending in a vertical direction, for example. First body portion 14 may also include a first curved surface 14c and a second curved surface 14d opposite the first curved surface 14c, for example. In some embodiments, the first and second curved surfaces 14c and 14d may extend between the first lateral surface 14a and the second lateral surface 14b. First body portion 14 may include a first implant cavity including a pair of spaced-apart arms 26, 28 that define, for example, a first receiving cavity 30 therebetween. In the illustrated embodiment, first receiving cavity 30 is configured for top loading of a spinal implant, such as, for example, first longitudinal rod 150, as shown in FIGS. 8A and 8B. However, in other embodiments, first receiving cavity 30 may be alternatively configured for side loading of a spinal implant.

Figure 6A:
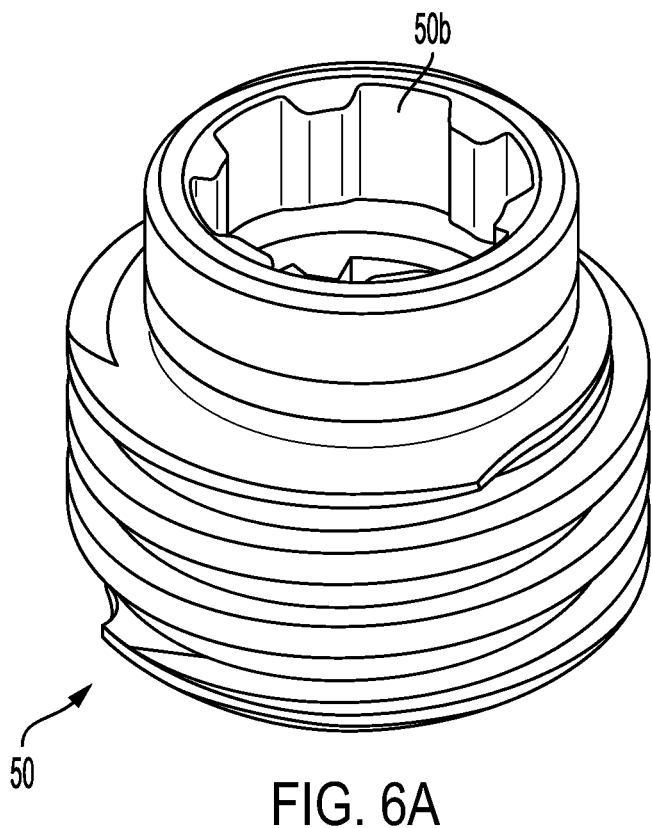
FIG. 6A is a perspective view of an example set screw for a spinal implant connector in accordance with the principles of the present disclosure.
Figure 6B:
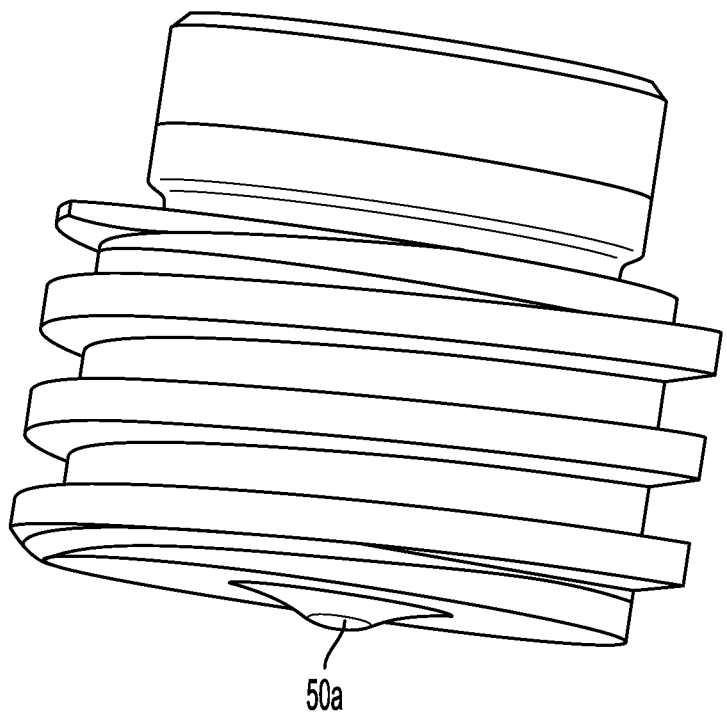
FIG. 6B is an alternate perspective view of an example set screw for a spinal implant connector in accordance with the principles of the present disclosure.
Figure 7:
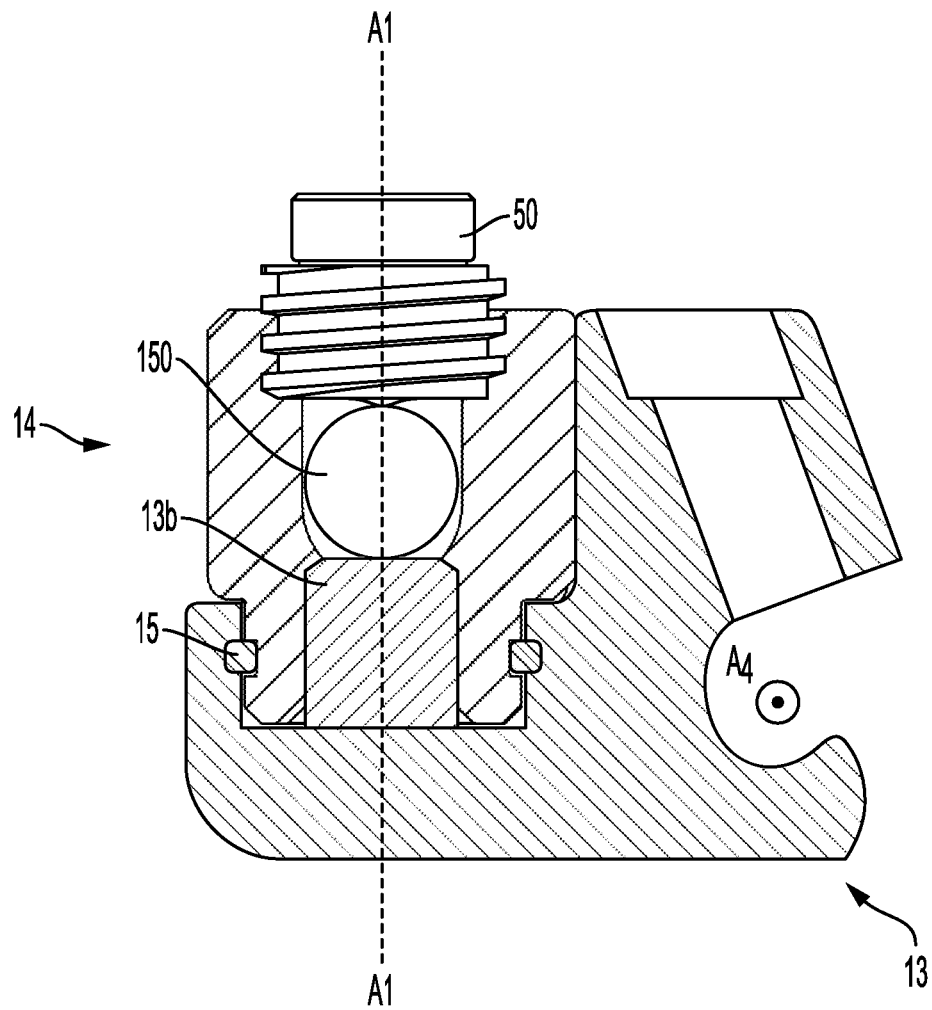
FIG. 7 is a cross sectional view of an example spinal implant connector in accordance with the principles of the present disclosure.

Arms 26, 28 may each be threaded on an interior surface and extend parallel to axis A1, as shown in FIG. 7. In some embodiments, arm 26 and/or arm 28 may be disposed at alternative orientations relative to axis A1, such as, for example, transverse and/or other angular orientations such as acute or obtuse, coaxial and/or may be offset or staggered. In some embodiments, axis A1 may define a trajectory for a corresponding set screw, e.g., set screw 50 illustrated in FIGS. 6A-6B. Arms 26, 28 may each include an arcuate outer surface, e.g., first curved surface 14c and second curved surface 14d. In some embodiments, at least one of the outer surfaces and the side surfaces of arms 26, 28 have at least one recess or cavity therein configured to receive an insertion tool, compression instrument and/or instruments for manipulating connector 12. In some embodiments, second body portion 13 may include at least one recess or cavity therein configured to receive an insertion tool, compression instrument and/or instruments for manipulating connector 12.

First receiving cavity 30 may comprise a first passageway for receiving a first longitudinal rod 150. In the illustrated embodiment, first receiving cavity 30 may be configured to adjustably orient a first longitudinal rod 150 in a plane substantially perpendicular to the first axis A1. For example, first body portion 14 may be rotatably coupled to second body portion 13 such that a first longitudinal rod 150 may freely rotate in a direction and/or plane that is substantially perpendicular to the first axis A1. For example, first longitudinal rod 150 may project and/or extend away from lateral surfaces 14a, 14b and first body portion 14 may freely rotate in place 360°. In other embodiments, first body portion 14 may be limited such that it will only rotate to a lesser extent, e.g., 270°, 180°, 90°, 45°, 35°, etc.

First receiving cavity 30 may include a curved bottom surface 30a defining, at least partly, a passageway for receiving a corresponding longitudinal rod 150. For example, curved bottom surface 30a may be defined, at least partly, by a segment of a circle having a radius that corresponds to an external radius of the first longitudinal rod 150 (in cross section). For example, an outer radius of the first longitudinal rod 150 may correspond to the curved bottom surface 30a such that a lower portion of first longitudinal rod 150 directly contacts bottom surface 30a.

In some embodiments, first receiving cavity 30 may include gripping elements or surfaces, such as, for example, one or more surfaces that are rough, arcuate, undulating, mesh, porous, semi-porous, dimpled and/or textured, to facilitate engagement with first longitudinal rod 150. Such features may increase a coefficient of friction or be used as an adhering surface in the use case an adhesive is additionally used, for example. As explained above, first receiving cavity 30 may define an axis A1 that extends parallel to arms 26, 28. In some embodiments, axis A1 may be disposed at alternate orientations, relative to arms 26, 28, for example, parallel, perpendicular and/or angular orientations such as acute or obtuse, coaxial and/or may be offset or staggered.

In the illustrated embodiment, first implant cavity 24 may include threaded surfaces 32 that define an opening 34 therebetween. Opening 34 may extend along an axis A1, as shown best in FIGS. 5A and 5B. Axis A1 is disposed in a substantially perpendicular orientation relative to axis A3. In some embodiments, axis A1 is disposed at alternate orientations, relative to axis A3, such as, for example, transverse and/or other angular orientations such as acute or obtuse, coaxial and/or may be offset or staggered. Opening 34 is disposed in communication with first receiving cavity 30 to facilitate fixation of first longitudinal rod 150 with connector 12.

Threaded surfaces 32 are configured for engagement with a coupling member, such as, for example, a set screw (see e.g., set screw 50 of FIGS. 6A-6B) to retain first longitudinal rod 150 within first receiving cavity 30. As illustrated in FIGS. 6A-6B, set screw 50 may include a drive interface 50b, for example, a hexalobular drive interface. Other embodiments may use other drive interfaces 50b, such as torx, square, hexagonal, polygonal, etc. Additionally, set screw 50 may include a protrusion 50a, for example. Protrusion 50a may be shaped like a hemisphere and may directly engage with a longitudinal rod 150 to retain it in place. In some embodiments, protrusion 50a may take alternate shapes. Example set screws may take any suitable form, type, or shape, e.g., a plain cup screw head, a knurled cup screw head, a flat screw head, an oval screw head, a cone screw head, a half-dog screw head, and a soft tipped screw head. In some embodiments, threaded surfaces 32 may be disposed with a corresponding set screw in alternate fixation configurations, such as, for example, friction fit, pressure fit, locking protrusion/recess, locking keyway and/or adhesive. In some embodiments, all or only a portion of surfaces 32 may have alternate surface configurations to enhance engagement with a spinal rod and/or a set screw such as, for example, rough, arcuate, undulating, mesh, porous, semi-porous, dimpled and/or textured.

Threaded surfaces 32 may receive a set screw 50 that may be disposable within first implant cavity 24 between a non-locking orientation and a locking orientation. In the non-locking orientation, first body portion 14 and longitudinal rod 150 are rotatable relative to second body portion 13. In the locked orientation set screw 50 is fully tightened along axis A1 and fixes the first body portion 14 relative to second body portion 13 and fixing an orientation of first longitudinal rod 150 with respect to connector 12. For example, when set screw 50 is fully tightened the first longitudinal rod 150 may be fixed relative to the first body portion 14 in a direction extending substantially parallel with a plane that is perpendicular with respect to Axis A1 and/or lateral surfaces 14a, 14b. For example still, in various embodiments a central longitudinal axis of the first longitudinal rod 150 may be exactly coextensive or substantially coextensive with axis A3 (at least the portion of first longitudinal rod 150 disposed within first receiving cavity 30 between lateral surfaces 14a, 14b).

Figure 4A:
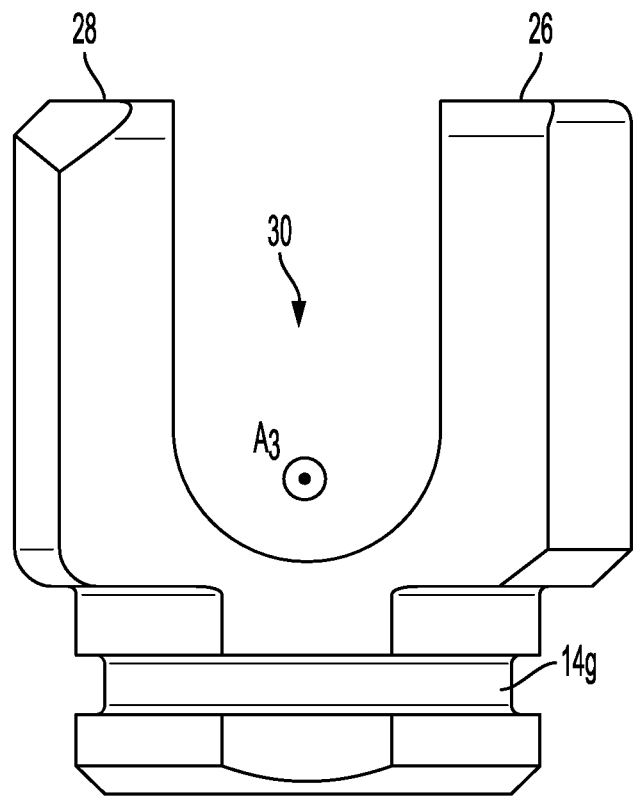
FIG. 4A is a perspective view of a first body portion of a spinal implant connector in accordance with the principles of the present disclosure.
Figure 4B:
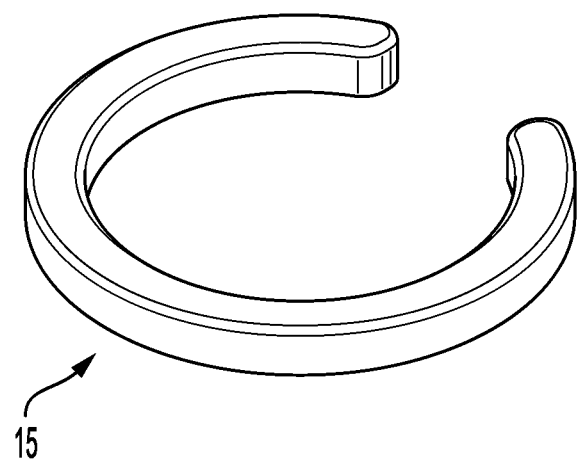
FIG. 4B is a perspective view of a retaining clip for a first body portion of a spinal implant connector in accordance with the principles of the present disclosure.

FIG. 4A shows an example embodiment where first body portion 14 may include a first groove 14g disposed proximate to a bottom portion 14h of first body portion 14. The first groove 14g may extend all the way around the first body portion 14. FIG. 4B illustrates a retaining clip 15, e.g., a spring clip or the like. Retaining clip 15 may be mated with first groove 14g. For example, first groove 14g may have an interior geometry that corresponds to the geometry of retaining clip 15. In the illustrated embodiment, first groove 14g and retaining clip 15 may include substantially planar sidewall surfaces, however, in other embodiments first groove 14g and retaining clip 15 may include curved sidewall surfaces, textured sidewall surfaces, and/or combinations of smooth and high friction sidewall surfaces.

Figure 5:
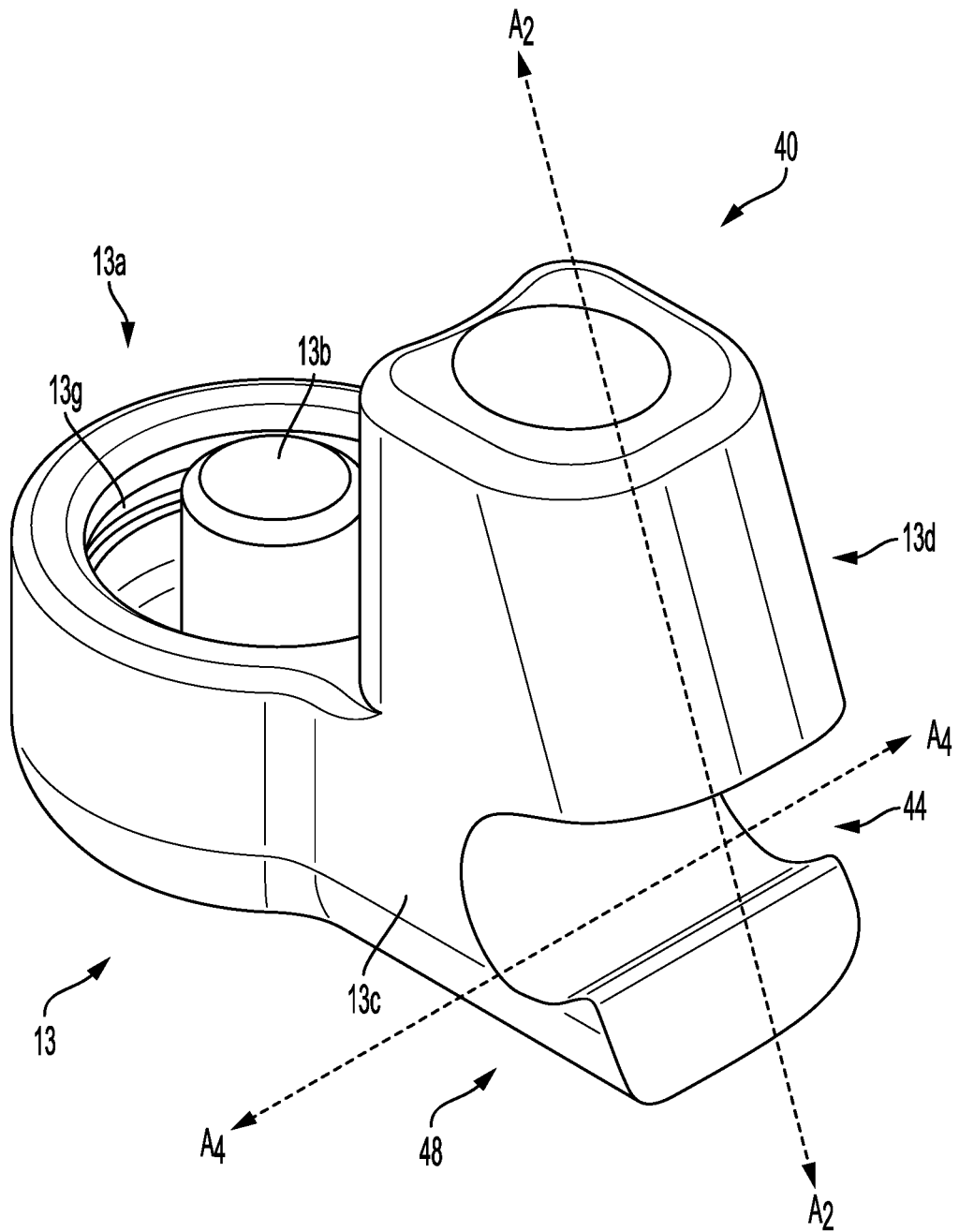
FIG. 5 is a perspective view of a second body portion of a spinal implant connector in accordance with the principles of the present disclosure.

FIG. 5 shows an example embodiment of second body portion 13. In the example embodiment, second body portion 13 may include second groove 13g, a channel 13a, and a column 13b. Second groove 13g may correspond to first groove 14g of first body portion. For example, second groove 13g may have the same, similar, or substantially the same dimensions as first groove 14g. Column 13b may be disposed in a central location of channel 13a, for example. A bottom portion of first body portion 14 may be inset inside of channel 13a and column 13b may extend through a corresponding aperture 14z of first body portion 14 (see FIG. 3). For example, a bottom portion of first body portion 14 may be shaped like a hollow cylinder, at least partly, and inset into a corresponding circular channel 13a and a centrally disposed column 13b may extends through aperture 14z, for example. At least one advantage of this structural arrangement is that first body portion 14 may freely rotate within channel 13a and around column 13b.

FIG. 7 illustrates an example cross section of connector 12 and shows first body portion 14 rotatably coupled to second body portion 13. In the example embodiment, first body portion 14 is disposed in channel 13a and column 13b extends through aperture 14z. Additionally, first body portion 14 is retained within channel 13a due to retaining clip 15 being mated with both first groove 14g and second groove 13g. In this way, retaining clip 15 may retain first body portion 14 vertically with respect to second body portion 13. At least one advantage of this arrangement is that the circular shaped surfaces of retaining clip 15, channel 13a, and column 13b may enable first body portion 14 to be operably coupled to second body portion 13. For example, in an arrangement that allows first body portion 14 to rotate in place 360° in a plane that is substantially perpendicular to axis A1. In operation, when set screw 50 is tightened along axis A1, set screw 50 may push down on longitudinal rod 150 thereby also pulling up first body portion 14 and placing retaining clip 15 under compression within first and second grooves 14g, 13g. Accordingly, when set screw 50 is fully tightened along axis A1, first body portion 14 and longitudinal rod 150 are fixed in position such that longitudinal rod 150 extends in a direction that is substantially parallel with a plane that is perpendicular to axis A1.

Figure 11:
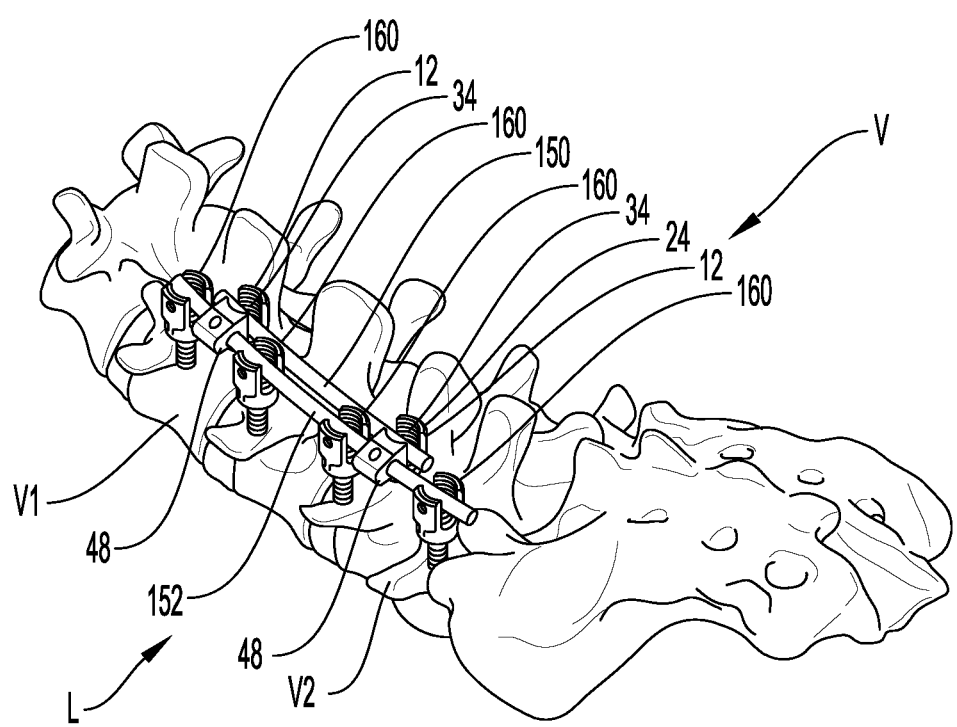
FIG. 11 is a perspective view of a spinal implant system including a plurality of connectors.

Referring back to FIG. 5, second body portion 13 may include a second implant cavity 44 that includes a second receiving cavity 48 that defines a passageway for a second longitudinal rod 152 (see FIG. 11). Second implant cavity 44 may include an arcuate configuration, such as, for example, a hooked shaped wall that defines a passageway that is configured to capture second longitudinal rod 152. Second implant cavity 44 may be configured to facilitate side loading of second longitudinal rod 152 with connector 12, for example.

In some embodiments, second receiving cavity 48 may have various cross section configurations, such as, for example, oval, oblong, triangular, rectangular, square, polygonal, irregular, uniform, non-uniform, variable and/or tapered. In some embodiments, surfaces of second receiving cavity 48 may include gripping elements or surfaces, such as, for example, rough, arcuate, undulating, mesh, porous, semi-porous, dimpled and/or textured to facilitate engagement with second longitudinal rod 152. Threaded opening 40 may define axis A2 and be configured to receive a set screw. Second receiving cavity 48 may define an axis A4 that extends away from lateral surfaces 13c, 13d. In some embodiments, axis A4 is disposed at alternate orientations, relative to axis A3, such as, for example, parallel, perpendicular and/or angular orientations such as acute or obtuse, coaxial and/or may be offset or staggered.

Second body portion 13 may further include a threaded opening 40 defining an Axis A2. Threaded opening 40 may be in communication with second receiving cavity 48 and be configured to receive a set screw (not illustrated). In various embodiments, threaded opening 40 may include a thread pitch 40t (see FIGS. 8B and 9B). In some embodiments, thread pitch 40t may be the same thread pitch, substantially the same thread pitch, or a similar thread pitch to opening 62 of U.S. patent application Ser. No. 16/395,498.

Axis A2 may be disposed off-angle with respect to axis A1, e.g., in a substantially non-perpendicular orientation relative to axis A1. In some embodiments, axis A2 may be disposed at alternate orientations, relative to axis A1, such as, for example, perpendicular, transverse, parallel, and/or other angular orientations such as acute or obtuse, coaxial and/or may be offset or staggered. Threaded opening 40 may be disposed in communication with second receiving cavity 48 to facilitate fixation of second longitudinal rod 152 with connector 12. For example, when the second longitudinal rod 152 may be fixed relative to the connector 12 in a direction extending substantially parallel with a plane that is perpendicular with respect to Axis A2 and/or lateral surfaces 13c, 13d. For example, in various embodiments a central longitudinal axis of the second longitudinal rod 152 may be exactly coextensive or substantially coextensive with axis A4 (at least the portion of second longitudinal rod 152 disposed within second receiving cavity 48 between lateral surfaces 13c, 13d).

Threaded opening 40 may be configured to receive any suitable type of set screw for fixing second longitudinal rod 152 in second receiving cavity 48 relative to connector 12. For example, a plain cup screw head, a knurled cup screw head, a flat screw head, an oval screw head, a cone screw head, a half-dog screw head, and a soft tipped screw head. At least one example set screw for threaded opening 40 may be seen as set screw 202 of U.S. patent application Ser. No. 16/395,498. Installation of second longitudinal rod 152 may include tightening a second set screw (not illustrated) in threaded opening 40 such that when the second set screw (not illustrated) is fully tightened the second longitudinal rod 152 is fixed relative to the second body portion 13 and/or connector 12. In some embodiments, longitudinal rod 152 may be fixed according to an alternate fixation configuration, such as, for example, friction fit, pressure fit, locking protrusion/recess, locking keyway and/or adhesive. In some embodiments, second receiving cavity 48 may have alternate surface configurations to enhance engagement with a spinal rod and/or a set screw such as, for example, rough, arcuate, undulating, mesh, porous, semi-porous, dimpled and/or textured.

FIG. 8A illustrates a perspective view of an example spinal implant connector 12. FIG. 8B illustrates a top down view of the example spinal implant connector of FIG. 8A. As shown by arrows in FIG. 8B, first body portion 14 may freely rotate with respect to second body portion 13. As explained previously, when set screw 50 is fully tightened, first longitudinal rod 150 may be fixed relative to connector 12.

Figure 9B:
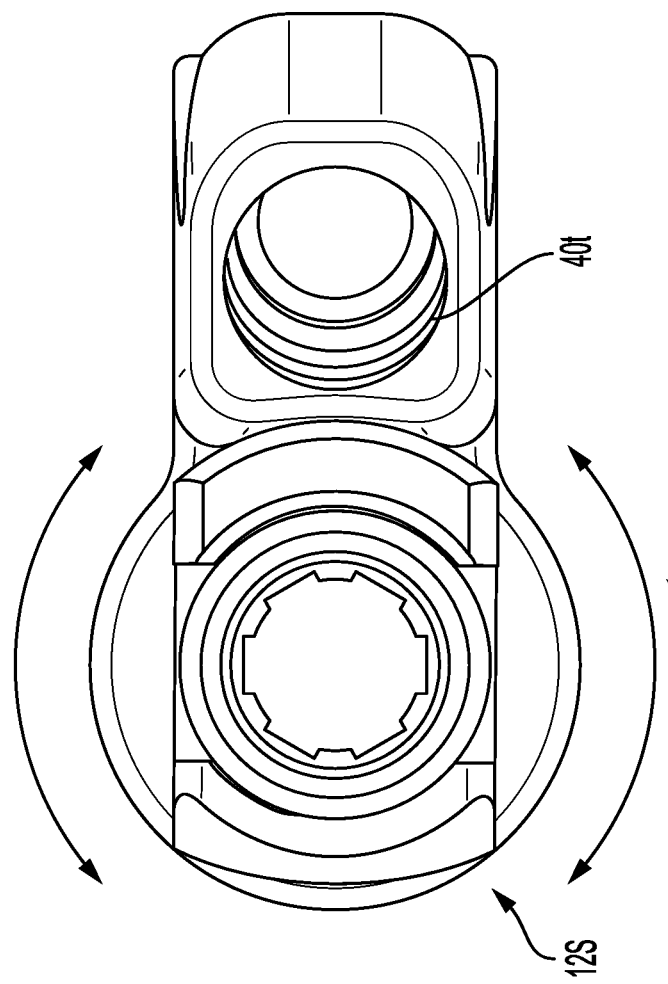
FIG. 9B is a top down view of the example spinal implant connector of FIG. 9A in accordance with the principles of the present disclosure.
Figure 9A:
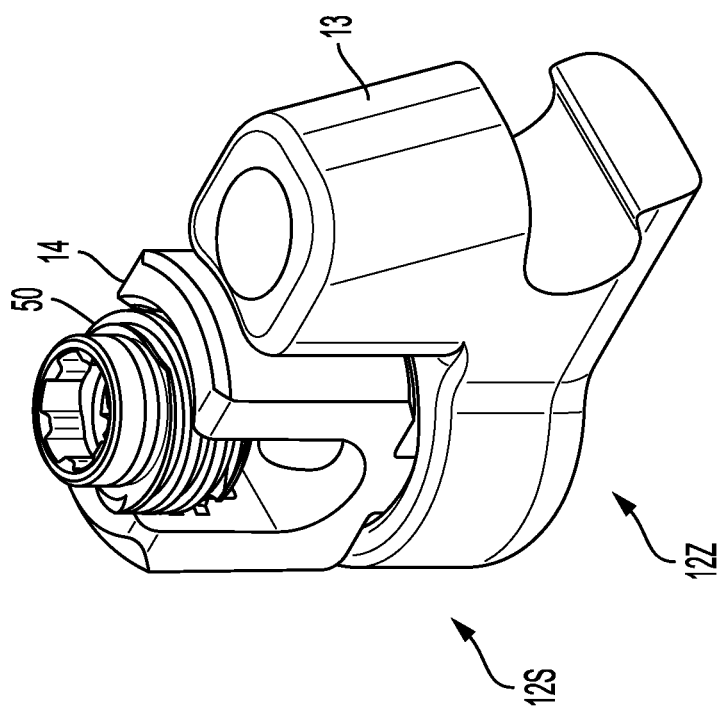
FIG. 9A is a perspective view of an example spinal implant connector in accordance with the principles of the present disclosure.
Figure 10A:
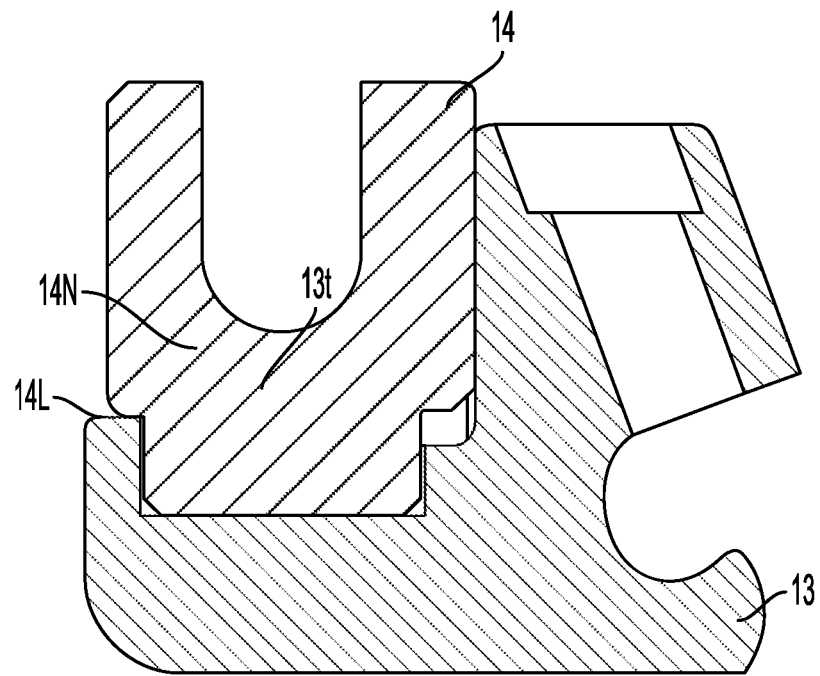
FIG. 10A is a cross section view of an example spinal implant connector in accordance with the principles of the present disclosure.
Figure 10B:
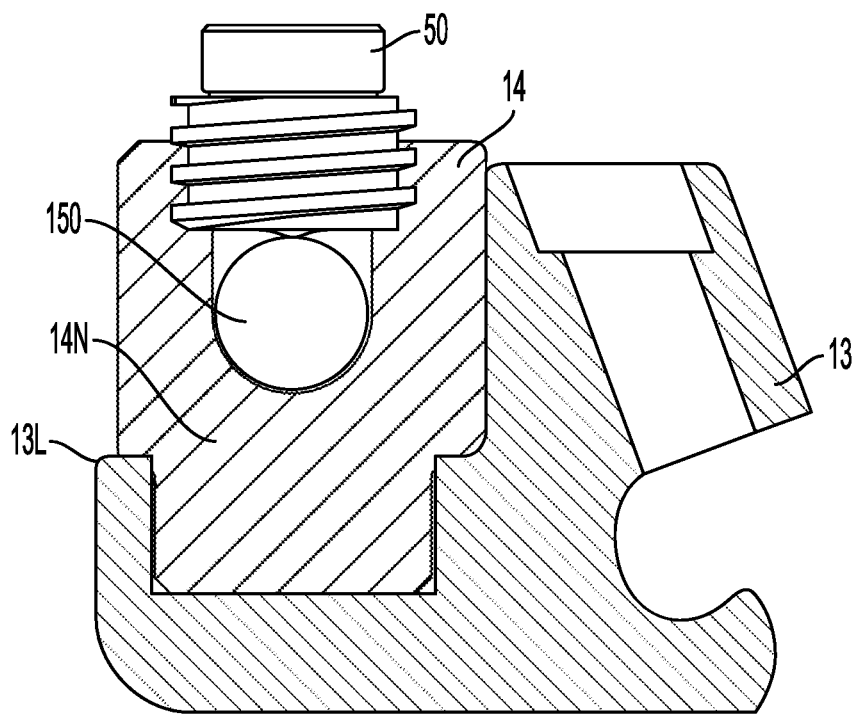
FIG. 10B is a cross section view of the example spinal implant connector of FIG. 10A after tightening a first set screw in accordance with the principles of the present disclosure.

FIG. 9A is a perspective view of an example spinal implant connector 12z. FIG. 9B is a top down view of the example spinal implant connector 12z of FIG. 9A. FIG. 10A is a cross section view of the example spinal implant connector 12z of FIGS. 9A-9B. FIG. 10B is another cross section of an example spinal implant connector 12z including a longitudinal rod 150 and set screw 50 for ease of understanding. It shall be appreciated that connector 12z may include the same, substantially the same, and/or similar components as connector 12 as explained above. Accordingly, duplicative description will not be repeated herein.

In the example embodiment, connector 12z may include a spline 12s. Spline 12s may include a plurality of ridges or teeth (male features) and a corresponding plurality of grooves (female features) configured for mating with the ridges or teeth. Spline 12s may provide an additional bearing surface to retain first body portion 14 relative to second body portion 13, for example. For example still, spline 12s may maintain an angular correspondence between first body portion 14 and second body portion 13 when the ridges or teeth are engaged with the corresponding grooves. In the example embodiment, spline 12s may comprise a plurality of teeth disposed on a lip portion 14L of first body portion 14 and a plurality of corresponding grooves disposed on a corresponding bearing surface 13L. In other embodiments, the location of the grooves and teeth may be reversed. For example, the teeth may be disposed on second body portion 13 and the grooves may be disposed on first body portion 14. In the disclosed embodiment, the teeth and/or grooves of spline 12s may extend along an arc of circle of about 270°. In other embodiments, the teeth and/or grooves of spline 12s may extend in a circular arrangement of about 360°. In the disclosed embodiment, the teeth and grooves may disposed evenly in about 5° increments, for example. In other embodiments, the teeth and grooves may be disposed evenly within a range of about 1° to about 10°.

Connector 12z may further include a positioning nut 14n and a corresponding threaded column 13t. Threaded column 13t may extend into an aperture 14z of first body portion 14. Positioning nut 14n may be tightened along threaded column 13t and provide a bearing surface to retain first body portion 14 vertically with respect to second body portion 13.

Referring to FIG. JOB, in operation, first body portion 14 may be nested with second body portion 13. First body portion 14 may be oriented to receive first longitudinal rod 150 in a desired orientation. Then, positioning nut 14n may be tightened along threaded column 13t. When positioning nut 14n is fully tightened, spline 12s may be fixedly engaged such that first body portion 14 may no longer rotate in place. After spline 12s is fixedly engaged and first body portion 14 is fixed, first longitudinal rod 150 may be placed through first implant cavity 24 and positioned within first receiving cavity 30. Thereafter, set screw 50 may be lighted along axis A1 and thereby fix first longitudinal rod 150 in the desired orientation.

As shown in FIG. 11, in some embodiments, spinal implant system 10 can include one or a plurality of connector(s) 12 and/or 12z (such as those described herein) and/or fixation elements, which may be employed with a single vertebral level or a plurality of vertebral levels. In some embodiments, connector(s) 12 and/or 12z may be engaged with vertebrae in various orientations, such as, for example, in series, in parallel, offset, staggered and/or alternate vertebral levels. In some embodiments, connector(s) 12 and/or 12z may be configured with multi-axial screws, sagittal angulation screws, pedicle screws, mono-axial screws, uniplanar screws, fixed screws, anchors, tissue penetrating screws, conventional screws, expanding screws and etc., for example. In some embodiments, connector(s) 12 and/or 12z may be employed with wedges, anchors, buttons, clips, snaps, friction fittings, compressive fittings, expanding rivets, staples, nails, adhesives, posts, connectors, fixation plates and/or posts, for example.

In assembly, operation and use, spinal implant system 10, may be employed with a surgical procedure, such as, for example, a correction treatment or revision treatment of an applicable condition or injury of an affected section of a spinal column and adjacent areas within a body. In some embodiments, spinal implant system 10 may be a completely or partially revised system based on a pre-existing system. In other embodiments, spinal implant system 10 may be an initially installed system, i.e., not a revision surgery technique based on a pre-existing system.

In use, to treat a selected section of vertebrae V, including vertebrae V1, V2, as shown in FIG. 11, a medical practitioner may obtain access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

In practice, an incision may be made in the body of a patient and a cutting instrument (not shown) may create a surgical pathway for implantation of components of spinal implant system 10. A preparation instrument (not shown) can be employed to prepare tissue surfaces of vertebrae V, as well as for aspiration and irrigation of a surgical region.

Bone screws 160 may be engaged with vertebrae V along a lateral side L of vertebrae V, as shown in FIG. 11. Bone screws 160 may be manipulated by a surgical tool to drive, torque, insert or otherwise connect bone screws 160 with vertebrae V. In some embodiments, connector 12 may be first fixedly connected to second longitudinal rod 152. Next, connector 12 may be connected to first longitudinal rod 150, for example as explained above. At least one advantage of disclosed connectors 12 and 12z is that first longitudinal rod 150 may be oriented in a different extension direction than second longitudinal rod 152. This arrangement may provide a surgeon with significantly greater range of possibilities for installation and connection between the first longitudinal rod 150 and second longitudinal rod 152. Additionally, it should be noted that first longitudinal rod 150 and second longitudinal rod 152 may be installed in any order and/or concurrently. In at least one embodiment, second longitudinal rod 152 is installed before first longitudinal rod 150. In an alternate embodiment, first longitudinal rod 150 is installed before second longitudinal rod 152.

First longitudinal rod 150 may be disposed with bone screws 160 along vertebrae V. Connectors 12 and/or 12z may be disposed adjacent first longitudinal rod 150 in any suitable location. In the illustrated embodiment, each connector 12 is manipulated to dispose first longitudinal rod 150 within first receiving cavity 30 from a top loading orientation. However, as mentioned previously, in other embodiment's first longitudinal rod 150 may be alternately configured and/or received in a different loading orientation.

First longitudinal rod 150 may be fixed within first receiving cavity 30 by engaging a corresponding set screw 50 with threads 32. The corresponding set screw 50 may be engaged with a surgical instrument, such as, for example, a driver (not shown), which advances the corresponding set screw 50 along axis A1 into engagement with first longitudinal rod 150 in a locking orientation. For example, a driver may engage a corresponding set screw 50 to fix first longitudinal rod 150 with first receiving cavity 30 and for attachment of first longitudinal rod 150 with vertebrae V.

Second longitudinal rod 152 may be disposed within second receiving cavity 48 from a side loading orientation. A corresponding set screw may be disposed within threaded opening 40 and tightened along axis A2. The corresponding set screw may be engaged with a surgical instrument, such as, for example, a driver (not shown), which may advance the corresponding set screw as described herein. For example, a driver may engage the corresponding set screw to fix the second longitudinal rod 152 with connector 12 and for attachment of second longitudinal rod 152 with vertebrae V. In some embodiments, second longitudinal rod 152 may be configured to share the load applied to first longitudinal rod 150. In some embodiments, second longitudinal rod 152 may be configured to extend first longitudinal rod 150 to an adjacent vertebral level. Second longitudinal rod 152 may be configured to add support and strength to spinal implant system 10 along vertebrae V. As mentioned previously, it shall be understood that first and second longitudinal rods 150, 152 may be installed in any order. Accordingly, the discussion above with respect to first and second longitudinal rods 150, 152 is equally applicable to both rods 150, 152.

In some embodiments, spinal implant system 10 includes a second set of connectors 12, bone screws 160 and spinal rods 150, 152 (not shown) delivered along the surgical pathway to the surgical site adjacent a contra-lateral side of vertebrae V. The second set of connectors 12, bone screws 160 and spinal rods 150, 152 may be connected with the contra-lateral side of vertebrae V, similar to lateral side L described herein. In some embodiments, the spinal constructs of spinal implant system 10, as described herein, are fixed with vertebrae V in a side by side orientation and/or a bi-lateral arrangement to stabilize vertebrae V and affect growth for a correction treatment to treat spine pathologies, as described herein. In some embodiments, one or more or all of the components of spinal implant system 10 can be delivered or implanted as a pre-assembled device or can be assembled in situ, in a selected order of assembly. Additionally or alternatively, the order of assembly of the particular components of spinal implant system 10 can be varied according to practitioner preference, patient anatomy or surgical procedure parameters.

Upon completion of a surgical procedure, the above disclosed surgical instruments, assemblies and non-implanted components of spinal implant system 10 may be removed from the surgical site and the incision may be closed. One or more of the components of spinal implant system 10 can be made of radiolucent materials such as polymers, for example. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

It will be understood that terms such as "same," "equal," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to emphasize this meaning, unless the context or other statements clearly indicate otherwise. For example, items described as "substantially the same," "substantially equal," or "substantially planar," may be exactly the same, equal, or planar, or may be the same, equal, or planar within acceptable variations that may occur, for example, due to manufacturing processes and/or tolerances. The term "substantially" may be used to encompass this meaning, especially when such variations do not materially alter functionality.

It will be understood that various modifications may be made to the embodiments disclosed herein. Likewise, the above disclosed surgical installation may be performed according to an alternate sequence. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
  a connector comprising a first body portion and a second body portion, the first body portion being rotatably coupled to the second body portion, the first body portion having a first implant cavity and the second body portion having a second implant cavity;
  the first implant cavity being defined, at least partly, by at least two threaded arm portions defining a first axis between the at least two threaded arm portions;
  the first implant cavity including a first receiving cavity configured to adjustably orient a first rod in a plane substantially perpendicular to the first axis; and
  the second implant cavity including a second receiving cavity configured to orient a second rod;
  wherein:
    the threaded arm portions are configured to receive a first set screw such that when the first set screw is fully tightened along the first axis the first rod is fixed relative to the first body portion in a direction extending substantially parallel with the plane,
    the second body portion further includes a threaded opening communicating with the second receiving cavity, the threaded opening defining a second axis and being configured to receive a second set screw such that when the second set screw is fully tightened the second rod is fixed relative to the second body portion,
    the first body portion further comprises an aperture disposed proximate a bottom surface of the first body portion,
    the second body portion further comprises a channel and a column, the column disposed proximate a central portion of the channel, and
    the column extends through the aperture and the bottom surface of the first body portion is disposed within the channel.

2. A spinal construct as recited in claim 1, wherein:
the first axis and the second axis extend in different directions, and
the first rod and the second rod are extendable in different directions.

3. A spinal construct as recited in claim 1, wherein:
the first axis and the second axis are disposed in a non-perpendicular orientation relative to one another, and
the first rod and the second rod extend in a non-perpendicular orientation relative to one another.

4. A spinal construct as recited in claim 1, further comprising: a retaining clip,
wherein:
the first body portion further comprises a first groove, the first groove being disposed proximate the bottom surface,
the second body portion further comprises a second groove, the second groove being disposed on an interior sidewall of the second body portion and facing the channel, and
the retaining clip is seated in the first groove and the second groove, the retaining clip rotatably coupling the first body portion and the second body portion.

5. A spinal construct as recited in claim 1, wherein the first body portion further comprises:
a first lateral sidewall and a second lateral sidewall opposite the first lateral sidewall, the first and second lateral sidewalls being substantially planar and extending in a vertical direction; and
a first curved sidewall and a second curved sidewall opposite the first curved sidewall, the first and second curved sidewalls extending between the first lateral sidewall and the second lateral sidewall,
wherein the first receiving cavity extends in a direction that is substantially perpendicular to the vertical direction.

6. A spinal construct, comprising:
a connector comprising a first body portion and a second body portion, the first body portion being rotatably coupled to the second body portion, the first body portion having a first implant cavity and the second body portion having a second implant cavity:
the first implant cavity being defined, at least partly, by at least two threaded arm portions defining a first axis between the at least two threaded arm portions;
the first implant cavity including a first receiving cavity configured to adjustably orient a first rod in a plane substantially perpendicular to the first axis; and
the second implant cavity including a second receiving cavity configured to orient a second rod;
wherein:
the threaded arm portions are configured to receive a first set screw such that when the first set screw is fully tightened along the first axis the first rod is fixed relative to the first body portion in a direction extending substantially parallel with the plane,
the second body portion further includes a threaded opening communicating with the second receiving cavity, the threaded opening defining a second axis and being configured to receive a second set screw such that when the second set screw is fully tightened the second rod is fixed relative to the second body portion,
the first body portion further comprises an aperture extending through a bottom surface of the first body portion,
the second body portion further comprises a channel and a threaded column, the threaded column disposed proximate a central portion of the channel, and
the threaded column extends through the aperture and the bottom surface of the first body portion is disposed within the channel.

7. A spinal construct as recited in claim 6, further comprising:
a nut, the nut being engaged with the threaded column and configured to retain the first body portion relative to the second body portion in the vertical direction.

8. A spinal construct as recited in claim 7, further comprising:
a spline,
wherein when the nut is fully tightened the spline fixedly engages the first body portion relative to the second body portion.

9. A spinal construct comprising:
a connector comprising a first body portion rotatably coupled to a second body portion, the first body portion including a plurality of teeth disposed on a lip portion, the second body portion including a plurality of grooves, the grooves corresponding to the plurality of teeth, the first body portion having a first implant cavity and the second body portion having a second implant cavity;
the first implant cavity being defined, at least partly, by at least two threaded arm portions defining a first axis between the at least two threaded arm portions;
the first implant cavity including a first receiving cavity configured to adjustably orient a first rod in a plane substantially perpendicular to the first axis; and
the second implant cavity including a second receiving cavity configured to orient a second rod;
wherein:
the threaded arm portions are configured to receive a first set screw such that when the first set screw is fully tightened along the first axis the first rod is fixed relative to the first body portion in a direction extending substantially parallel with the plane, and
the second body portion further includes a threaded opening communicating with the second receiving cavity, the threaded opening defining a second axis and being configured to receive a second set screw such that when the second set screw is fully tightened the second rod is fixed relative to the second body portion,
the first body portion further comprises an aperture extending through the bottom surface of the first body portion,
the second body portion further comprises a channel and a threaded column, the threaded column disposed proximate a central portion of the channel, and
the threaded column extends through the aperture and the bottom surface of the first body portion is disposed within the channel.

10. A spinal construct as recited in claim 9, wherein the plurality of teeth are arranged symmetrically with respect to one another on the lip portion.

11. A spinal construct as recited in claim 10, wherein the plurality of grooves are arranged in segment of a circle and symmetrically disposed with respect to one another on the second body portion.

12. A spinal construct as recited in claim 9, wherein:
the first axis and the second axis extend in different directions, and the first rod and the second rod are extendable in different directions.

13. A spinal construct as recited in claim 9, wherein:
the first axis and the second axis are disposed in a non-perpendicular orientation relative to one another, and
the first rod and the second rod extend in a non-perpendicular orientation relative to one another.

14. A spinal construct as recited in claim 9, wherein the first body portion further comprises:
a first lateral sidewall and a second lateral sidewall opposite the first lateral sidewall, the first and second lateral sidewalls being substantially planar and extending in a vertical direction;
a first curved sidewall and a second curved sidewall opposite the first curved sidewall, the first and second curved sidewalls extending between the first lateral sidewall and the second lateral sidewall,
wherein the first receiving cavity extends in a direction that is substantially perpendicular to the vertical direction.

15. A spinal construct as recited in claim 9, further comprising:
a nut, the nut being engaged with the threaded column and configured to retain the first body portion relative to the second body portion in the vertical direction.

16. A spinal construct system comprising:
at least one anchoring member configured to couple to a corresponding pedicle screw;
a plurality of connectors, each connector comprising a first body portion and a second body portion, the first body portion being rotatably coupled to the second body portion, the first body portion having a first implant cavity and the second body portion having a second implant cavity;
each first implant cavity being defined, at least partly, by at least two corresponding threaded arm portions defining a corresponding first axis between the at least two corresponding threaded arm portions;
each first implant cavity including a corresponding first receiving cavity configured to adjustably orient a first rod in a range of extension directions substantially perpendicular to the first axis; and
each second implant cavity including a corresponding second receiving cavity configured to orient a second rod;
wherein:
each of the corresponding threaded arm portions are configured to receive a corresponding first set screw such that when the corresponding first set screw is fully tightened along the corresponding first axis the first rod is fixed relative to the corresponding first body in a direction comprising the range of extension directions, and
each second body portion further includes a corresponding threaded opening communicating with the corresponding second receiving cavity, each threaded opening defining a corresponding second axis and being configured to receive a corresponding second set screw such that when the corresponding second set screw is fully tightened the second rod is fixed relative to the corresponding body,
the first body portion further comprises an aperture disposed proximate a bottom surface of the first body portion,
the second body portion further comprises a channel and a column, the column disposed proximate a central portion of the channel, and
the column extends through the aperture and the bottom surface of the first body portion is disposed within the channel.

17. A spinal construct system as recited in claim 16, further comprising:
a spline, a nut, and a threaded column,
wherein when the nut is fully tightened the spline fixedly engages the first body portion relative to the second body portion.

* * * * *